(12) United States Patent
Schmidt et al.

(10) Patent No.: US 7,456,953 B2
(45) Date of Patent: Nov. 25, 2008

(54) METHOD AND APPARATUS FOR IMPROVED LIGHT DISTRIBUTION IN AN ANTI-RESONANT WAVEGUIDE SENSOR

(75) Inventors: Oliver Schmidt, Aalen (DE); Michael Bassler, Menlo Park, CA (US); Peter Kiesel, Palo Alto, CA (US); Patrick Y Maeda, Mountain View, CA (US); Noble M Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 11/777,976

(22) Filed: Jul. 13, 2007

(65) Prior Publication Data

US 2008/0013877 A1  Jan. 17, 2008

Related U.S. Application Data

(63) Continuation-in-part of application No. 10/976,434, filed on Oct. 29, 2004, now Pat. No. 7,268,868.

(51) Int. Cl.
*G01J 3/30* (2006.01)
*G01N 21/64* (2006.01)

(52) U.S. Cl. .................... 356/317; 356/417; 250/458.1; 385/12

(58) Field of Classification Search ................ 356/317, 356/417
See application file for complete search history.

(56) References Cited

FOREIGN PATENT DOCUMENTS

EP  05110121  5/2006
JP  2005306837  5/2006

*Primary Examiner*—F. L Evans
(74) *Attorney, Agent, or Firm*—Kent Chen

(57) ABSTRACT

An improved method of analyzing target analytes in a sample is described. The method is based on creating an approximately homogeneous distribution of light in an anti-resonant guided optical waveguide to improve light-target interaction in a target-containing medium. The light-target interaction can be monitored by many different means to determine characteristics of the target analyte.

22 Claims, 16 Drawing Sheets

| REFRACTIVE INDEX OF ANALYT n | ANGLE γ' (DEGREES) | ANGLE γ'' (DEGREES) |
|---|---|---|
| 1.00 | 48.2 | - |
| 1.05 | 45.6 | - |
| 1.10 | 42.8 | - |
| 1.15 | 39.9 | 74.4 |
| 1.20 | 36.9 | 64.2 |
| 1.25 | 33.6 | 56.0 |
| 1.30 | 29.9 | 48.4 |
| 1.35 | 25.8 | 40.8 |

US 7,456,953 B2

METHOD AND APPARATUS FOR IMPROVED LIGHT DISTRIBUTION IN AN ANTI-RESONANT WAVEGUIDE SENSOR

CROSS-REFERENCE TO RELATED APPLICATIONS

This application is a continuation-in-part of U.S. patent application Ser. No. 10/976,434, filed Oct. 29, 2004 now U.S. Pat. No. 7,268,868, which is hereby incorporated by reference.

BACKGROUND

The detection of micro-organisms for medical treatments and security systems has taken on increased importance in recent years. Modern medical systems as well as security systems depend on the detection and identification of microorganisms, including bioagents or toxins in the air, food, water, blood or other specimens.

Conventional detection is usually done in the laboratory. Laboratory testing typically uses skilled personnel in a time consuming process. Portable versions of laboratory PCR (polymerase chain reaction) have been developed, however, these devices are bulky and not cost effective.

Optical systems for detecting and identifying micro-organisms provide numerous advantages over chemical and other analysis techniques. For example, optical systems can reduce or eliminate the need for field workers to use chemical reactions to detect elements. Optical systems are also often non-destructive to the sample being analyzed.

Most optical biosensor designs rely on interactions between light and a biological sample to provide information on sample characteristics. However, the interaction between light and biological elements in the sample is typically weak. Thus without amplification of the interaction, a large quantity of analyte may be needed. Obtaining such large sample sizes may not be practical for many applications.

In order to increase the interaction between light and biological elements in the sample, optical waveguides may concentrate the intensity of light on the sample. In one use, microorganisms in the sample reside in liquid immediately adjacent to a waveguide surface. Evanescent waves from the waveguide interact with the molecules of the biological elements. However, the interaction between the evanescent waves and the biological elements is still weaker than desired.

A related patent application entitled Anti-resonant waveguide sensors, U.S. patent application Ser. No. 10/976,434 by many of the same inventors and assigned to the same assignee describes an improved sensor system and is hereby incorporated by reference. The patent application describes using an anti-resonant waveguide to confine and guide the light within the target-containing medium and therefore increase the interaction region between light and analyte (e.g., biological or chemical agent) being tested. The described system has a number of uses including the detection of binding events.

However, the system has not performed as well as expected. In particular, the light distribution within the anti-resonant waveguide is not as uniform as desired for many applications. Furthermore, in some applications, significant portions of the waveguide need to be devoted to coupling the light and uniformly distributing the light through the waveguide.

Thus an improved system for detection and identification with minimized light coupling region and homogeneous light distribution is needed.

SUMMARY

A method of analyzing a sample is described. The sample includes a fluid medium (e.g., gas, aerosol or liquid) carrying certain target analytes (e.g., toxins, bacteria or their spores), viruses, mammalian or insect cells, parasites, oocytes, or certain chemicals). The method places the sample to be analyzed between a first layer/medium and a second layer/medium. The sample has a sample index of refraction that is less than the indexes of refraction of the first and second layer/medium. A beam of light enters the sample at an angle such that an anti-resonant guided optical waveguide (ARGOW) mode propagates through the sample. Anti-resonance waveguides enable a strongly enhanced interaction between light and analyte. Furthermore, the waveguide is designed to insure an approximately homogeneous light distribution throughout the fluidic channel using waveguide coupling and beam shaping techniques. This is useful for many different characterization methods. The interaction between photons in the anti-resonant mode and target analyte (e.g. biological molecules) in the sample is monitored to determine a characteristic of molecules in the sample.

DETAILED DESCRIPTION

An improved sensor that enhances interaction between light and target analytes in a sample is described. Light from a light source is coupled into a sensor chamber, such as a microfluidics channel filled with the sample. The light may be subject to processing by lenses, coupling structures or other techniques to generate an almost homogenous distribution of light in the sample. As used herein, "almost homogenous" or "approximately homogenous" is defined to mean that the intensity of light from the light source varies by no more than 50% through most (greater than 80%) of the sample volume after the initial coupling structures. More typically, the intensity of light from the light source is adjusted to vary by no more than 25% through most of the sample volume.

As the light enters the sample, the angle of light entry into the sensor chamber is carefully controlled to generate anti-resonant modes in the sample. The anti-resonant modes allow the sample itself to serve as an optical waveguide resulting in increased interaction between the target molecules and the light.

Figure 1:
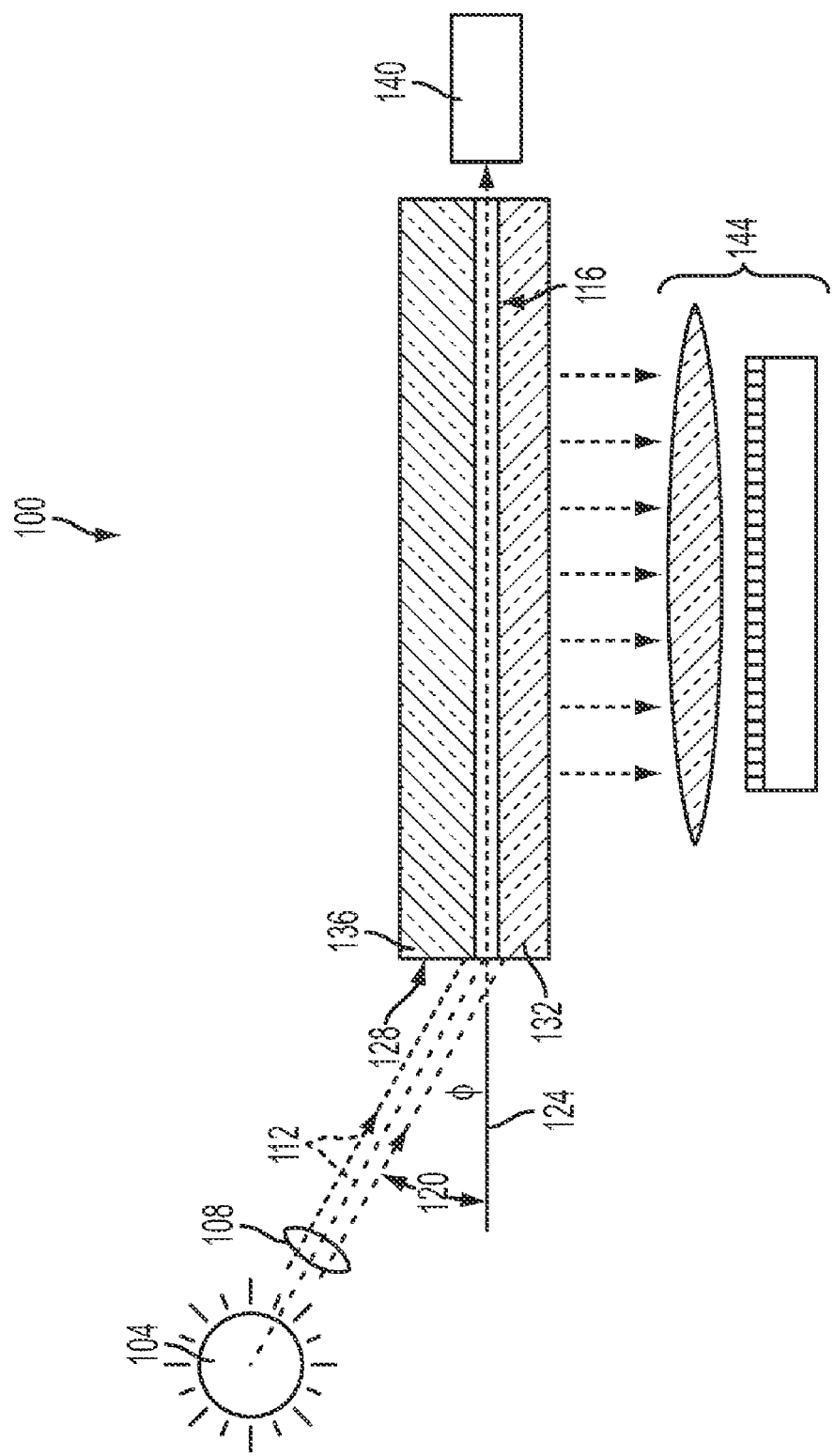
FIG. 1 shows a side sectional overview of an analysis system.

FIG. 1 shows a side view of one embodiment of the optical sensing system 100. In FIG. 1, a light source 104 and/or a lens system 108 directs a light beam 112 into a sample 116. Depending on the test being conducted, light in light beam 112 may be of coherent or incoherent. When coherent light is used, light source 104 is typically a laser. In other cases white light or light emitting diodes may be used.

Light beam 112 enters sample 116 at an angle of incidence 120. As used herein, reference to the word "light", "light beam" and "optical" is should be broadly interpreted to include a broad range of frequencies including ultraviolet, visible, infrared, and far infrared radiation as well as terahertz radiation. As used herein, the angle of incidence is the angle with respect to a normal 124 of the surface 128. The angle of incidence is carefully selected such that an anti-resonant guided optical wave (ARGOW) or mode of light can be set up within sample 116.

Sample 116 is typically a thin film of liquid carrying the target analyte (e.g., biological molecules) to be analyzed. Sample 116 may also be a gas or an aerosol carrying the analyte to be analyzed. If the sample is a gas or aerosol, sealing materials around the perimeter of the chamber containing the sample keeps the gas between substrate 132 and covering layer 136. Sample 116 thickness is usually kept larger than the wavelength of light being used to analyze the sample.

Substrate 132 and covering layer 136 border sample 116 sides. Substrate 132 and covering layer 136 are typically made from a transparent material such as glass. In one embodiment, glass slides are used for substrate 132 and covering layer 136. The index of refraction of the substrate and covering layer are slightly higher than that of the sample 116 to facilitate generation of an anti-resonant wave in sample 116. An example index of refraction of substrate 132 and covering layer 136 might be between 1.4 and 1.8 while the index of refraction of a liquid sample 116 might be between 1.2 and 1.4 although as will be explained, a wide range of other indices are also possible.

The actual conditions used to create an anti-resonant guided optical wave (ARGOW) propagating through a sample sandwiched between two higher index materials may be found by computing the Eigensolutions of the Helmholtz equation for a plane wave propagating along a slab waveguide structure. A general Helmholtz equation for the electric field E is given by:

$$(\nabla^2 + |\vec{k}|^2)E = 0; \quad \text{(Eq. 1)}$$

$$|\vec{k}| = |\vec{k}_0| \cdot n$$

Assuming a plane wave that propagates along a x-direction within a slab waveguide structure, and confining the wave with respect to the z-orientation results in the following solution to the Helmholtz equation:

$$E = \tilde{E}(z) \cdot e^{i(k_x x - \omega t)}; \frac{\partial E}{\partial y} = 0 \quad \text{(Eq. 2)}$$

where E denotes the electric field, $\tilde{E}(z)$ its z-dependence, $k_x$ the x-component of the wavevector. $\vec{k}_0$ is the lights vacuum wave vector and n the materials refractive index.

In this case the Helmholtz equation reduces to:

$$\left(\frac{\partial^2 E}{\partial z^2} + k_0^2 \cdot n^2(z)\right)\tilde{E}(z) = k_x^2(z) \cdot \tilde{E}(z). \quad \text{(Eq. 3)}$$

The Eigensolutions $\tilde{E}(z)$ can be characterized by $k_x$, or for convenience by a so called effective refractive index $n_{\mathit{eff}}$ defined as:

$$n_{\mathit{eff}} \equiv \frac{k_x}{|\vec{k}_0|} \quad \text{(Eq. 4)}$$

In the previously described slab index guided waveguide structure, the equations above can be numerically solved resulting in a large number of Eigen solutions $\tilde{E}(z)$. These Eigensolutions are called optical modes. Equations 3 and equation 4 also enable computation of the respective refractive indices $n_{\mathit{eff}}$ and modal confinement factors $\Gamma$ of these modes.

Figure 6:
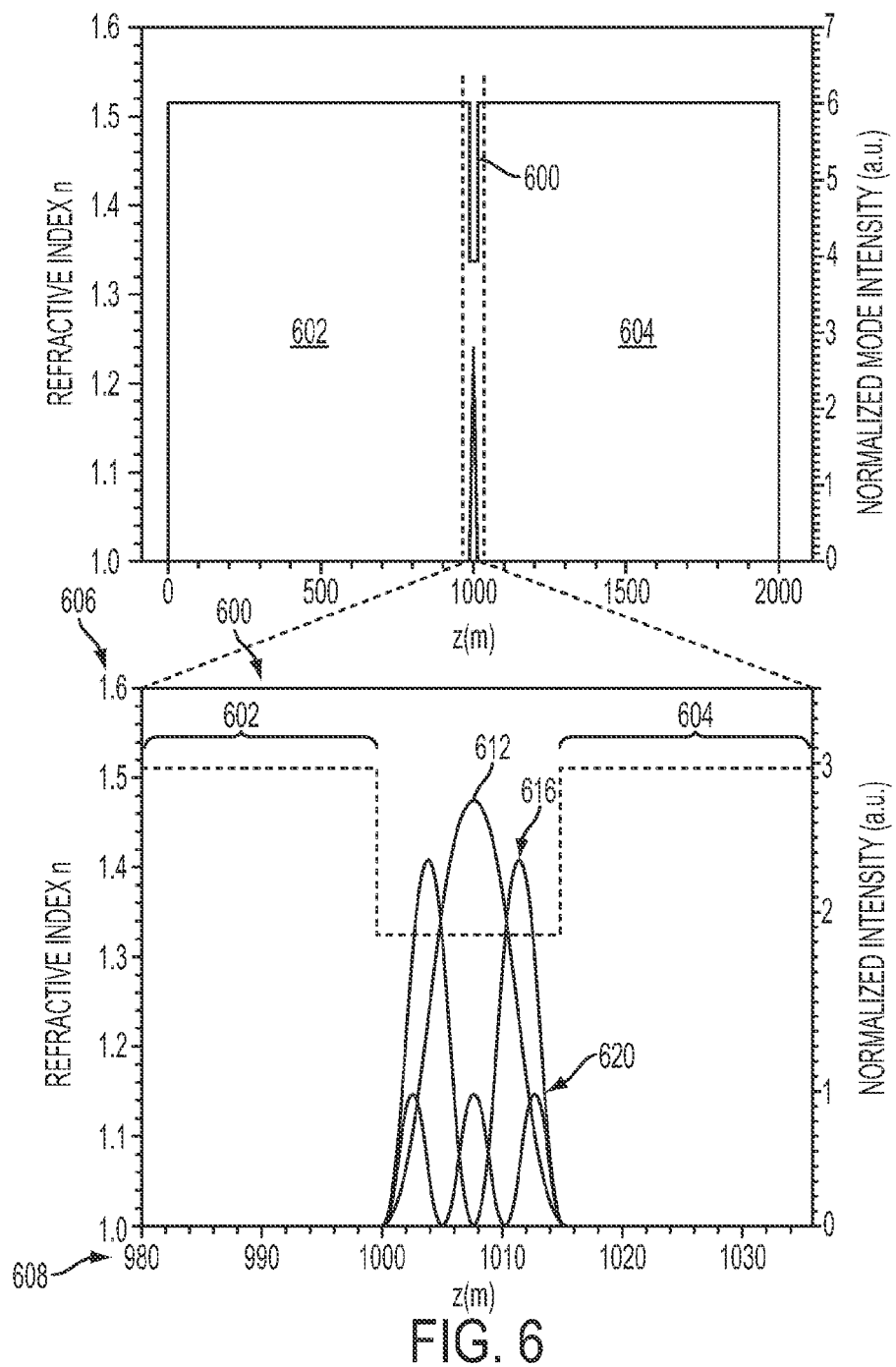
FIG. 6 shows an intensity profile of various anti-resonant modes in an example analyte cross section.

FIG. 6 shows examples of optical modes. In FIG. 6, anti-resonant intensity patterns 612, 616, 620 are plotted across a cross section of a liquid sample 600 placed between glass plates 602, 604. Typical indexes of refraction across the sample are provided along y axis 606. A distance along sample 600 is provided on x axis 608. An example first optical mode is shown by normalized intensity pattern 612, a second optical mode is shown by normalized intensity pattern 616 and a third optical mode is shown by normalized intensity pattern 620.

A confinement factor $\Gamma$ corresponds to the fraction of the light intensity confined in the waveguide core. For maximum interaction between target molecules in the sample and the light beam, the sample or analyte itself serves as the waveguide core. The core is surrounded by a cladding layer, typically the portion of the medium immediately adjacent to the sample. In future references to the cladding, the "cladding layer" shall refer to a portion of the medium that lies immediately on either side of the sample. The thickness of the cladding layer can be chosen within a wide range but the typical thickness is a several wavelengths of the light propagating in the medium.

In the case of "anti-resonant" waveguides, herein defined to be a waveguide in which the core has a lower refractive index than the cladding layer, a number of optical modes with reasonably large confinement factors, up to and past 90%, can be found. These modes (or Eigensolutions) are characterized by effective refractive indices $n_{eff}$ close to (typically slightly smaller than) the refractive index n of the core layer material. When the core thickness is large compared with the wavelength of propagating light, the $n_{eff}$ of these modes of interest, approaches the refractive index of the core n.

$$d_{core} \gg \lambda \Rightarrow n_{eff} \approx n \quad \text{(Eq. 5)}$$

Figures 2, 3:
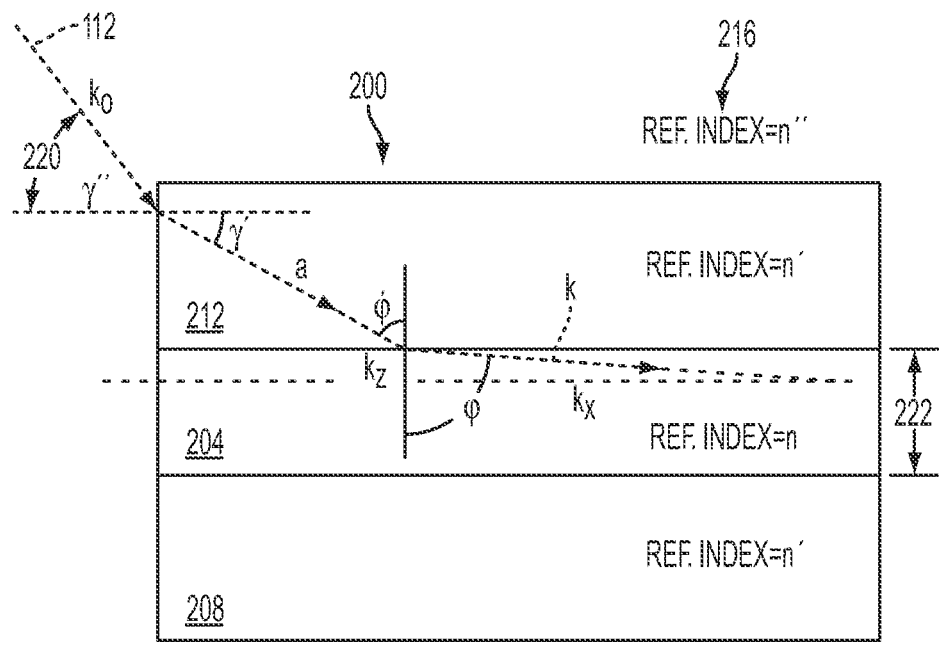
FIG. 2 shows an expanded side sectional view of a waveguide receiving an input light beam with a target-containing sample as a core.
FIG. 3 is a table showing example incidence angles for different analytes surrounded by a glass cladding.

Each Eigenmode can be excited by directing a beam of light at the waveguide at a specific angle of incidence. The angle of incidence corresponds to the effective refractive index $n_{eff}$. FIG. 2 shows one geometry of a slab waveguide 200 where the refractive index of the analyte 204 is n, the refractive index of substrate 208 and cover layer 212 are n' and the refractive index of the surroundings 216 is n". The optimum angle of incidence $\gamma(n_{eff})$ 220 for the structure of FIG. 2 may be derived as follows:

$$\sin(\varphi) = \frac{k_x}{k} = \frac{n_{eff}}{n}; \quad \text{(Eq. 6)}$$
$$\sin(\varphi') = \frac{n}{n'}\sin(\varphi) = \frac{n_{eff}}{n'};$$
$$\cos(\gamma') = \cos(90° - \varphi') = \sin(\varphi');$$
$$\gamma' = \arccos\left(\frac{n_{eff}}{n'}\right);$$
$$\sin\gamma'' = \frac{n'}{n''}\sin\gamma';$$
$$\gamma'' = \arcsin\left(\frac{n'}{n''}\arccos\left(\frac{n_{eff}}{n'}\right)\right);$$

When analyte 204 thickness 220 (typically waveguide core diameter $d_{core} \approx 10 \ldots 100$ μm) is large compared with the wavelength of the incident light ($\lambda = 0.3 \ldots 2$ μm) the approximation of (Eq.5) is acceptable. Using the equation 4 approximation allows substitution of analyte refractive index n for effective refractive index $n_{eff}$. The substitution results in an angle of incident that depends only on the refractive indices of the analyte, the core layer and the outside world:

$$\gamma'' = \arcsin\left(\frac{n'}{n''}\arccos\left(\frac{n}{n'}\right)\right); \quad \text{(Eq. 7)}$$

An example of a typical set of refractive indices might be an analyte of water with an n=1.34, a glass cladding layer with an n'=1.5 and an air or vacuum surrounding with n"=1. Using a glass cladding in an air surrounding for an example, the table in FIG. 3 lists appropriate angles of incident γ" in order to generate an ARGOW mode based on the sample or analyte refractive indexes.

Figure 4:
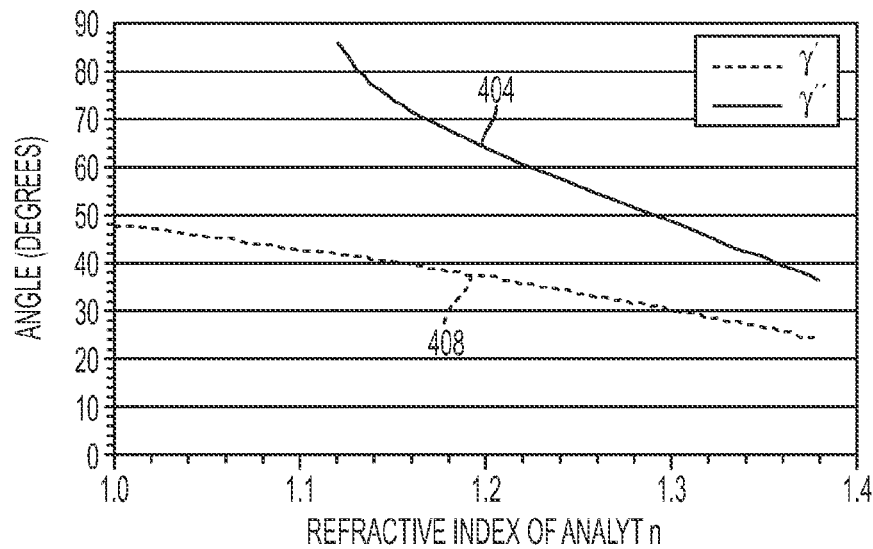
FIG. 4 is a chart that plots an angle of incidence into the waveguide structure of FIG. 2 as a function of the index of refraction of the sample.

FIG. 4 plots the data shown in FIG. 3. As shown in curve 404 of FIG. 4, the angle of incidence increases with decreases in the sample refractive index. At sample refractive indices less than 1.15 (n<1.15), it is very difficult to couple light into the waveguide facette and generate desired anti-resonant modes. Even for n>1.15, the optimum angles for generating anti-resonant modes are still larger than what may be suitable for coupling large amounts of light into the sample. Large angles create difficulties because these angles force the use of smaller diameter beams to hit the facette at the large angles. Furthermore, the use of large angles substantially increases reflection losses.

Figure 5:
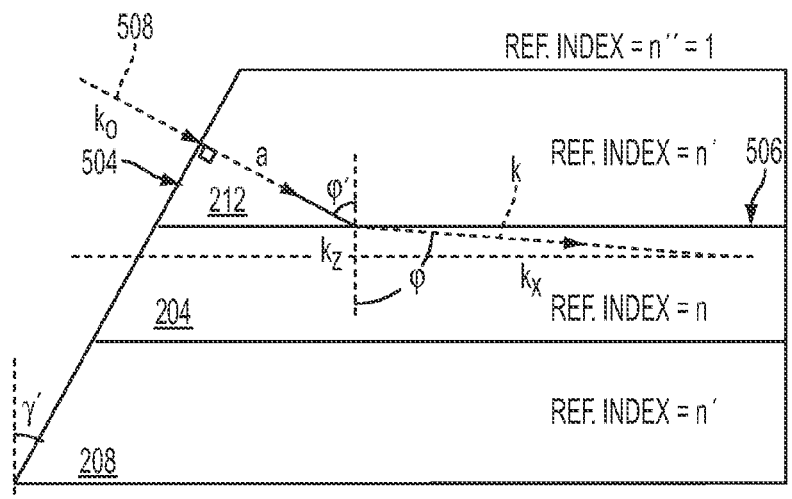
FIG. 5 shows a side sectional view of a waveguide with a biological sample as a core and with a tilted entrance facette.

FIG. 5 shows an alternate structure of FIG. 2 that minimizes losses caused by large incident angles. In FIG. 5, the entrance facette 504 is tilted. Reflections at the facette are minimized when incidence beam 508 perpendicularly enters entrance facette 504. By adjusting the tilt angle γ' such that a beam perpendicularly enters facette 504 and still strikes the cladding and sample interface 506 at an angle ϕ' suitable to create an anti-resonant mode, reflections from the facette can be minimized while still generating the desired anti-resonant modes.

Table 3 shows tilt angles γ' for the structure of FIG. 5 that corresponds to various analyte refractive indexes. By tilting the entrance facette 504, generation of anti-resonant optical waves in analytes with refractive indices that range down to n=1 becomes possible. Generating anti-resonant optical waves in low index samples enables the use of gas and aerosol samples. Note that in this case the refractive index of the surrounding medium n" might be chosen smaller than the refractive index of the medium n in order to also allow higher anti-resonant waveguide modes to be guided with reasonable leakage loss.

Although two geometries and end facette designs have been provided in FIG. 2 and FIG. 5, these geometries are provided for example only. It is possible to use other geometries and end facette designs to couple light into an anti-resonant propagating wave. Examples of other geometries include curved end facettes and cylindrical sample shapes rather than the angular end facettes and slab structures described. How to couple light into these other geometries in order to generate an anti-resonant wave in the sample can be determined by solving, either mathematically or numerically the general Helmholtz equation for these geometries. Such calculations are known to those of skill in the art. Thus the scope of the invention should not be limited to the particular example analyzed herein.

Figure 7:
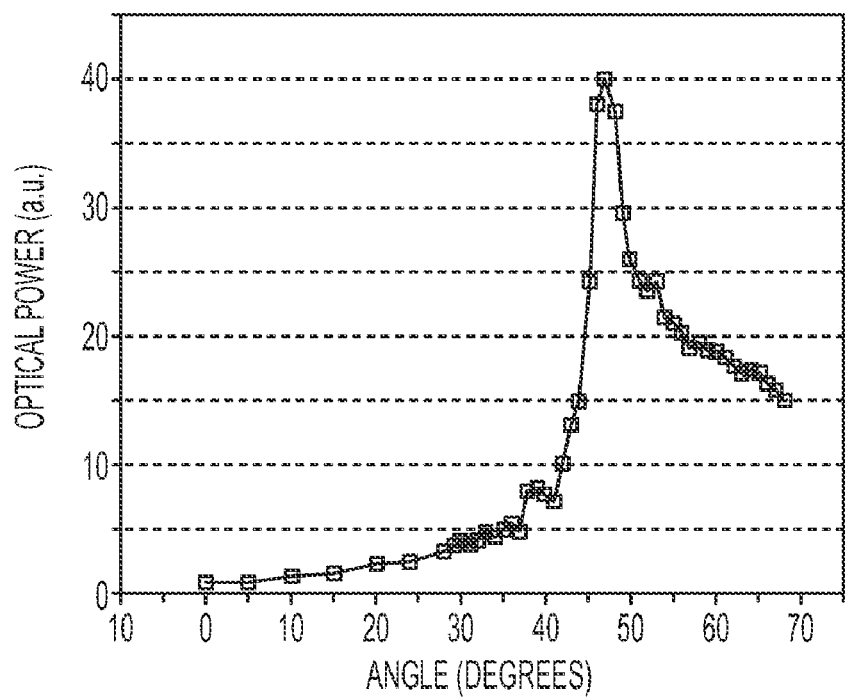
FIG. 7 shows the fluorescence intensity as a function of the coupling angle of the excitation light.

FIG. 7 is a plot of the actual florescent intensity output from a sample as a function of a coupling angle of excitation light into the sample. As will be described, the experimentally generated results of FIG. 7 match closely the theoretical expected coupling efficiencies at various angles of light input.

In order to generate the graph of FIG. 7, excitation light from a single blue high powered LED was coupled at various angles into a side of a liquid film placed between two glass slides. The excitation light excited a fluorescein dye in the liquid film and resulted in fluorescence throughout the entire film area (an area of 25×75 mm$^2$). The resulting fluorescence was then measured.

In the measurements, the measured fluorescence intensity per unit area was similar to that which has been obtained by perpendicularly (from the top) focusing the total excitation power from the LED onto a small spot (e.g. 3×3 mm$^2$) in the sample. The improved fluoresce results from a more efficient use of the excitation light by coupling the light into an ARGOW, in particular, guiding the light between the glass slides. This compares favorably to regular fluorescence detection when the excitation light is input perpendicular to the sample plane and results in transmission of most of the light. Using anti-resonant waveguide excitation the sample itself guides the excitation light between the glass slides providing a long interaction length between light and fluorescent molecules. FIG. 7 plots the fluorescence intensity as a function of the coupling angle of the excitation light. The experimental value for optimum coupling efficiency is in excellent agreement with the theoretically predicted value.

FIG. 6 shows the refractive index profile and the normalized mode intensity of 3 anti-resonant modes of a glass/water/glass anti-resonant waveguide. The anti-resonant modes are calculated assuming 480 nm wavelength light and a 15 μm thick liquid film between two glass slides. The predicted confinement factors for these modes within the liquid film are quite large. For the first three modes confinement factors of Γ=0.9, 0.8 and 0.55 respectively were obtained.

Each mode can be specifically excited by adjusting the incidence angle +(the angle 120 of FIG. 1). The anti-resonant modes with the highest confinement factors can be excited at a glancing angle φ=46.5°. Glass cladding thickness variations will usually not affect this angle because glass thicknesses are large compared with the wavelength of the propagating light (even if infrared light is used). Changes in liquid film thickness can change the optimum incidence angle; however, calculations show that the effect is very small. Reducing the thickness of the liquid film from 15 μm to 5 μm changes the optimum glancing angle φ from about 46.5° to only about 46.6°. Because within a window of about 0.5 degree, there is available a number of modes with reasonably high confinement factors, the slight change in optimum glancing angle does not present difficulties for the actual system.

Changes in light wavelength also produces slight changes in optimum incidence angle. For example, substituting infrared light (~1500 nm) for blue light (~480 nm) only changes the optimum incidence angle by about 1.8°. The difference in the dispersion of glass and water has a larger influence compared to the different confinement conditions for the different wavelengths which have only small impact on incidence angle.

Figure 8:
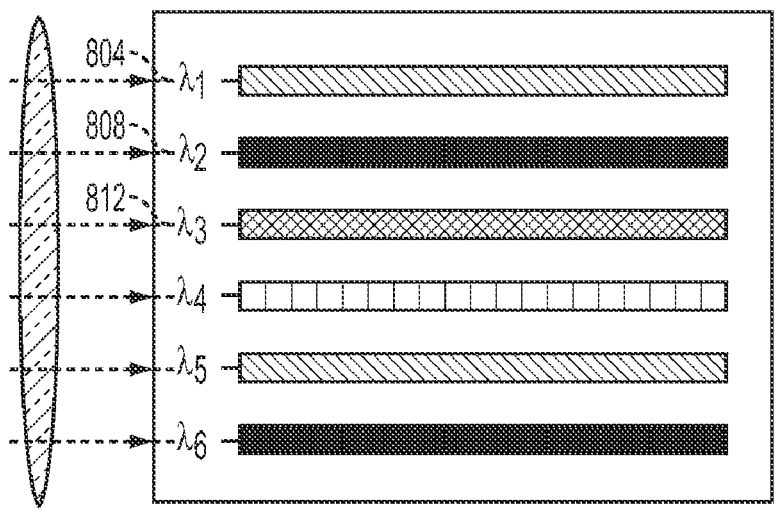
FIG. 8 shows a top view of a system to process in parallel different tests on a sample to determine the presence of a target analyte

The ability of the overall system to accommodate changes in light frequency and sample thickness makes it ideal for use in parallel analytic techniques. These are particularly useful in sophisticated systems where several different tests are to be conducted in parallel to determine the composition or presence of various target analytes. FIG. 8 shows a top view of a sample 800 receiving several frequencies of light 804, 808, 812 at once. Each frequency of light could correspond to a different test to be performed on the sample.

Figure 9:
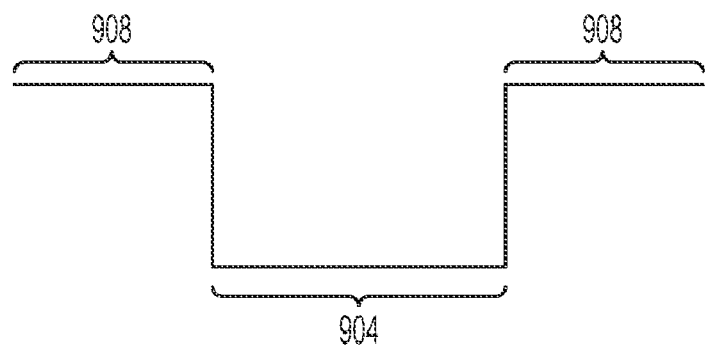
FIGS. 9-14 show sample index profiles of a sample and cladding immediately adjacent the sample.

In the preceding discussion, analysis has been done on step index profiles such as that shown in FIG. 9. However, the generation of ARGOWs should not be limited to such index profiles. FIGS. 9-14 show other index profiles where an index of refraction through the cladding and sample is plotted along a vertical axis and the distance along a cross section of the cladding and sample is plotted along a horizontal axis. As was previously explained, the thickness of the cladding layers is not critical and can be chosen within a wide range. Depending on the application and method of forming the cladding, the thickness of the cladding in one example embodiment is approximately 1 mm (e.g. if glass slides are used). In other cases the cladding may be chosen very thin, not more than three or four wavelengths of the propagating light.

Figure 10:
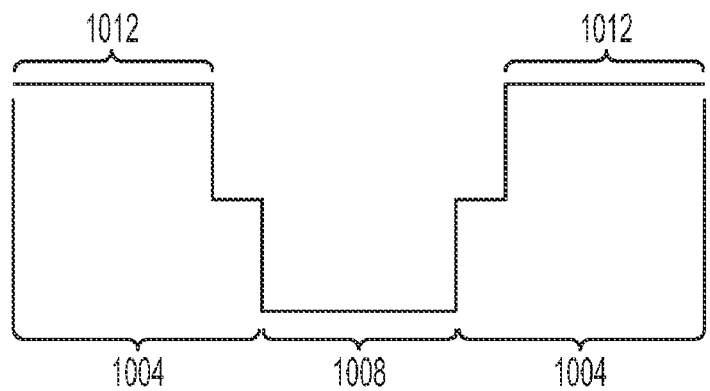

FIG. 10 shows a two step function where cladding region 1004 surrounding sample region 1008. Cladding region 1004 includes two steps in the index of refraction. Systems where a coating is used to prevent sticking of the analyte or other parts of the sample to the sample chamber or medium walls might exhibit such an index of refraction profile. For example, a teflon coating used in cladding region 1004 to coat a glass medium might be a typical example. Teflon has an index of refraction of 1.38 between the glass medium 1012 index of refraction (about 1.44) and a water based sample index of refraction.

Figure 11:
Figure 12:
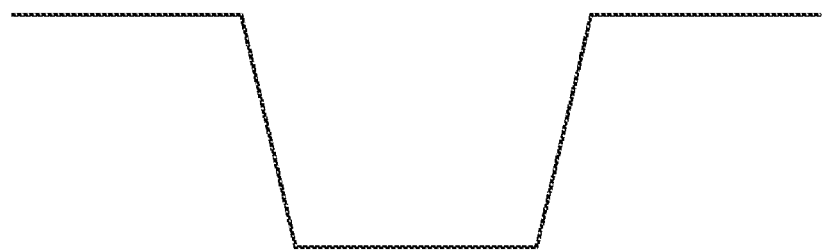
Figure 13:
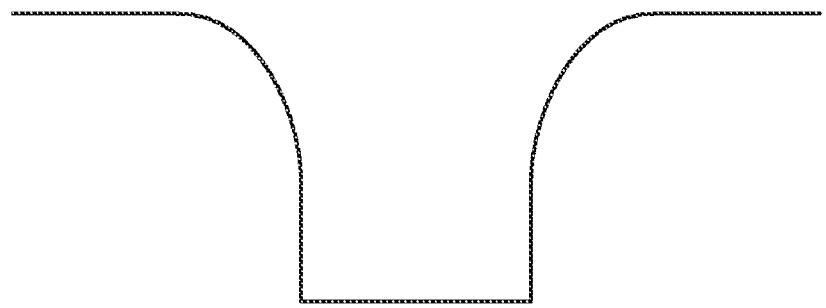
Figure 14:
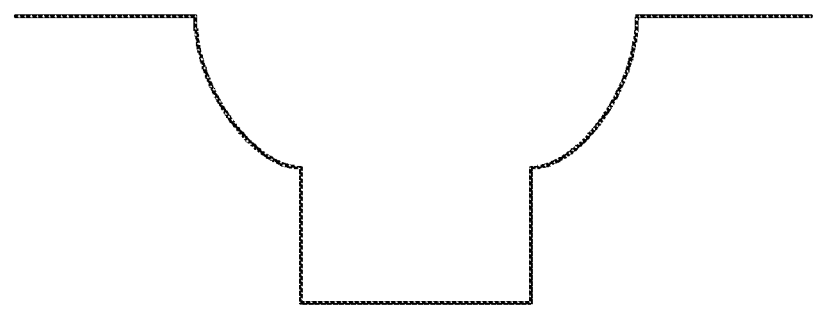

FIG. 11 shows that the sample itself does not have to have a constant index of refraction. FIG. 11 shows a parabolic index of refraction profile that may be exhibited by a fluid sample flowing at different speeds through a medium (e.g. causing phase separation of a mixture). Other monotonically increasing indexes of refraction (monotonically increasing from the edge of the sample through the cladding layer) are shown in FIGS. 12-14. Monotonically increasing indexes of refraction through the cladding region minimizes reflections that may occur from the cladding layers.

Figure 15:
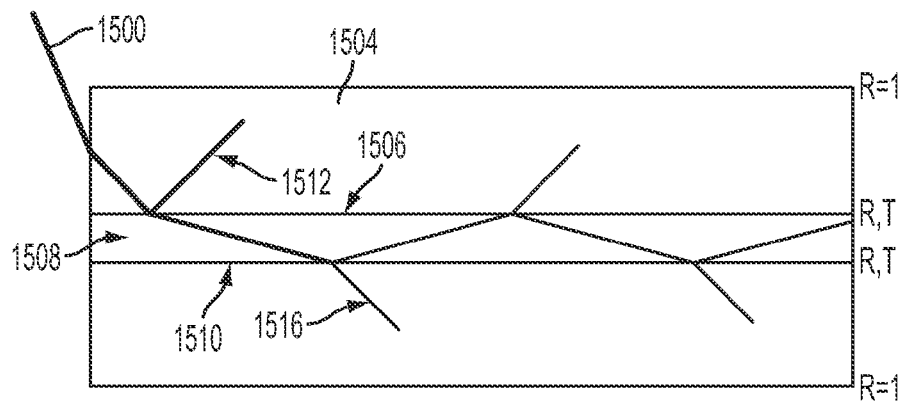
FIG. 15 shows the interaction of light between a fluid sample and a glass top layer and a glass bottom layer.
Figure 16:
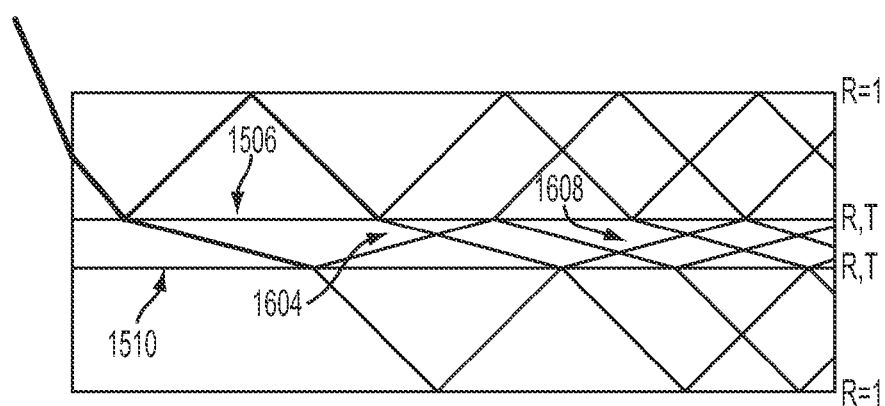
FIGS. 16-17b shows the effect of multiple reflections between a fluid sample and a glass top layer and a glass bottom layer and the effect on the intensity distribution in the fluid sample.
Figure 17A:
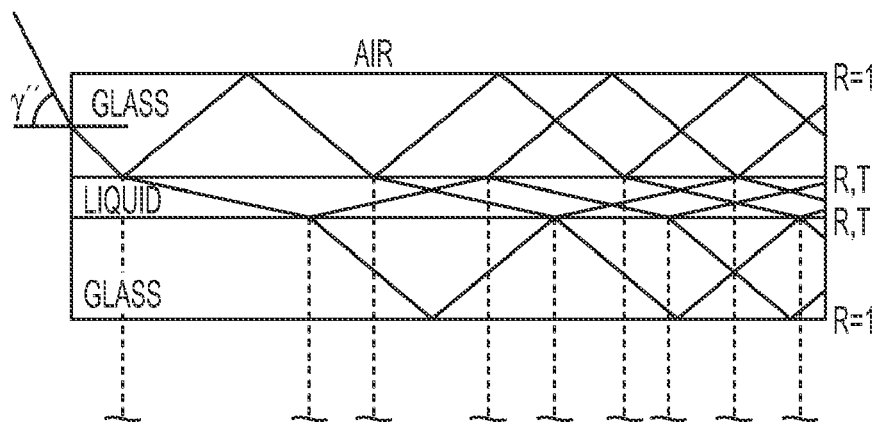
Figure 17B:
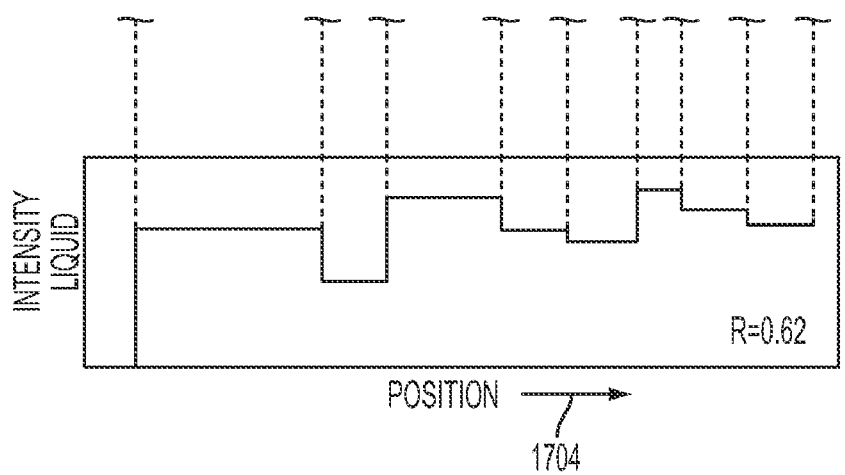

Cladding layer reflections need to be carefully controlled. One of the factors that determines sensing system performance is the homogeneity of light distribution throughout the analytic fluid. FIG. 15 shows an example beam of light 1500 entering a cladding 1504, in this example glass, and refracting into a liquid sample 1508 being tested. In the illustrated embodiment, light beam 1500 loses some intensity to reflection 1512 at the glass-liquid interface 1506. Light is also lost to transmission beam 1516 at second glass-liquid interface 1510. Transmission losses continue at each reflection along the glass-liquid interfaces 1506, 1510. FIG. 16 shows all of the "lost light" is returned via reflections at the cladding outer edge. For example, light rays 1604, 1608 feed light back into the fluid layer from these outer edge reflections. FIG. 17b shows an intensity profile in the sample fluid as a function of position. As shown in FIG. 17b, the light intensity gradually becoming more uniform or "approximately homogeneous" as the light reflections average out along axis 1704.

In general, an almost constant light intensity along the sample is preferred. Reaching the constant light intensity in as short a distance as possible minimizes the need for larger sample sizes. An approximately homogeneous light distribution is especially important for fluorescence spectroscopy where the spectral information is collected as particles pass the wavelength detector. Inhomogeneous excitation can produce incorrect spectral information. Although sensing systems can compensate for minor variations in light intensity, significantly inhomogeneous light distribution in the sample can result in unacceptably wide variations of the light output originating from the particle-light interaction. Thus, the data may be too severely impacted to allow for spectral characterization.

Figure 18:
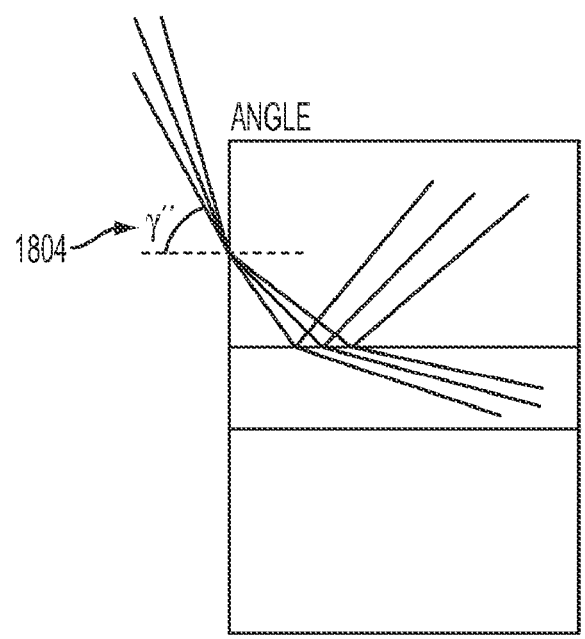
FIG. 18 shows introducing light at various angles to improve the distribution of light in a fluid sample.
Figure 19:
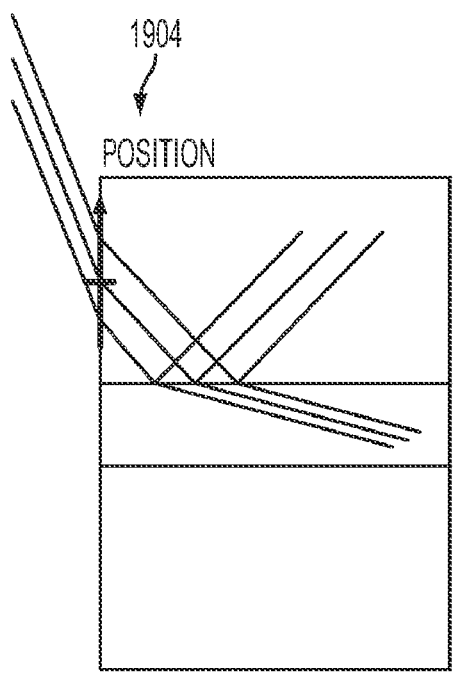
FIG. 19 shows introducing light at a variety of positions to improve the distribution of light in a fluid sample.
Figure 28:
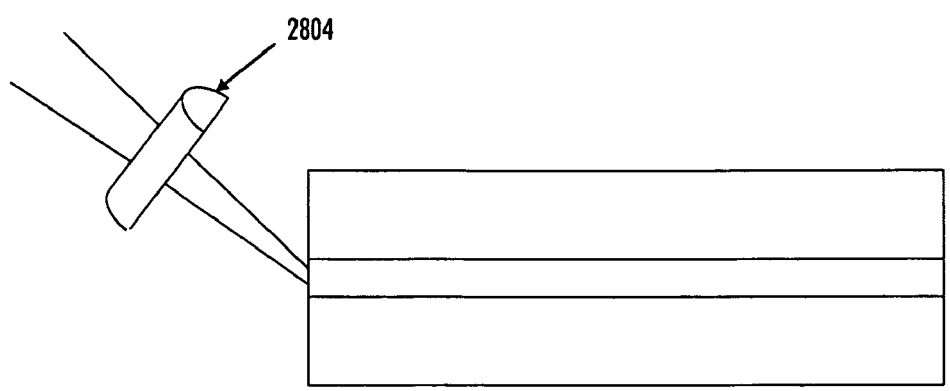
FIG. 28 shows an example lens for use in directing light into a sample.

FIG. 18 shows one method of averaging light by coupling the light into the channel over a range of angles 1804. The FIG. 18 embodiment may be achieved by using a lens system to approximately focus the light at the point of entry. Alternately, FIG. 19 shows a broad beam similar to a plane wave being introduced over a large area 1904. A lens system may be used to generate the broad beam. One example of a lens system is a cylindrical lens as shown in FIG. 28. A cylindric lens or a lens with two different focal lengths is favorable in situations where the beam has to be parallel in the plane of the channel and an angle spectrum is desired perpendicular to the channel to improve coupling efficiency.

Figure 20:
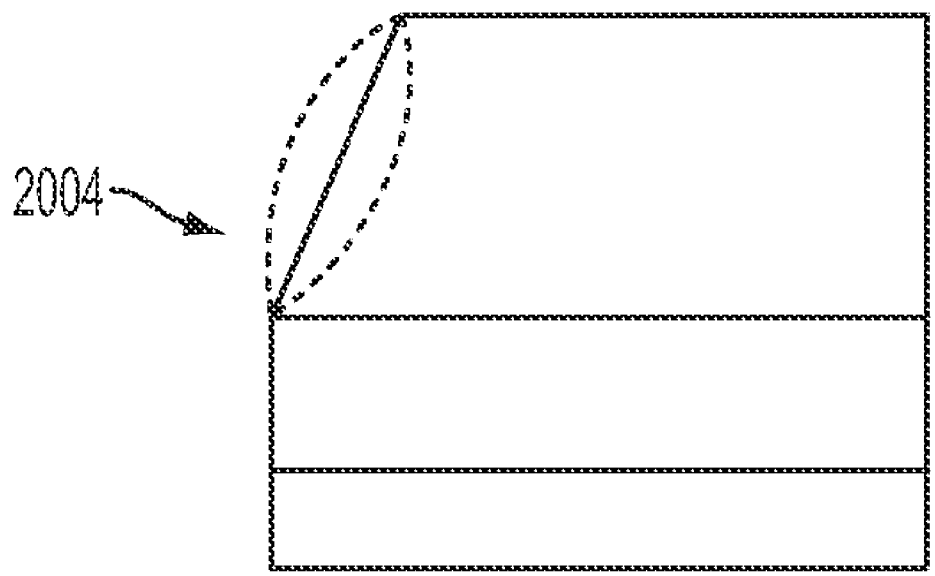
FIG. 20 shows curving an entrance facet in which light will enter to improve the distribution of light entering a sample.

FIG. 20 shows an embodiment that avoids complicated lens systems by curving the entrance region 2004 of the cladding layer where the light enters the cladding. The curved entry facet which may be concave or convex, serves as an "integrated lens" that spreads light entering the facet such that the light distribution simulates the spreading illustrated in FIG. 18. The spreading beam covers a larger area of the sample cladding interface helping to achieve an approximately homogeneous light distribution in the sample over a shorter distance from the entry facet.

Figure 21:
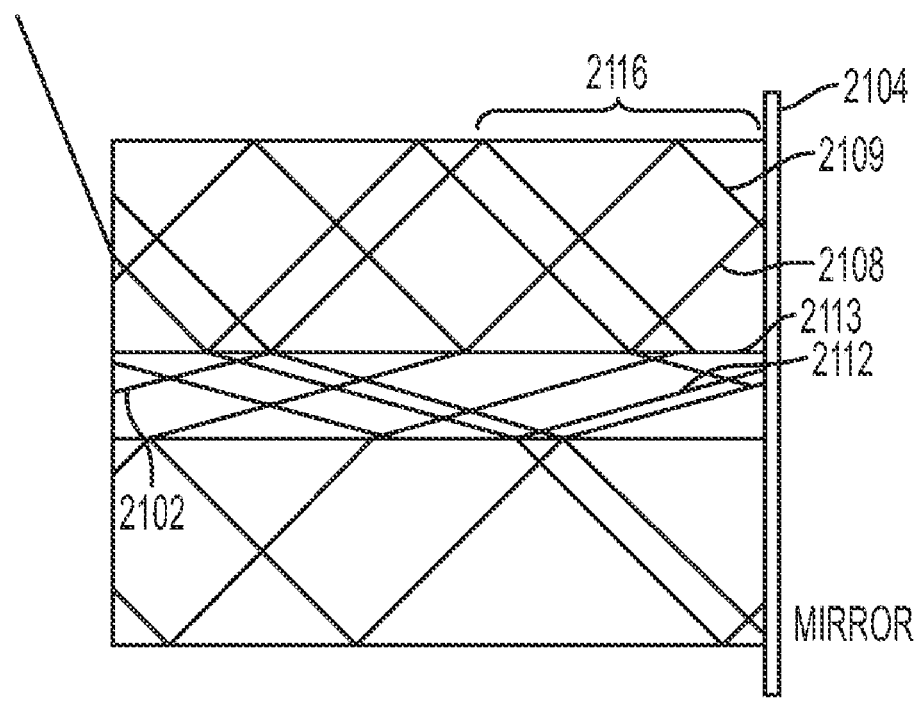
FIGS. 21-23 show applying mirrors at various positions to improve the distribution of light in a sample.

After light enters the sample, various media in the fluid absorb the light resulting in a reduced light intensity towards the "back end" of the sample opposite the "front end" where the light from the light source first enters the fluid. In the illustrated embodiment (FIG. 21), a highly reflecting surface such as mirror 2104 may be applied to an end of the sample opposite or furthest from the front end where light from the light source first enters the sample. As used herein, a highly reflective surface is defined as a surface that reflects at least 80% of the incident light intensity while a metallic mirror on glass typically reflects at least 95% of the incident light intensity. In the illustrated embodiment, mirror 2104 reflects incident light rays 2108, 2112 and returns them back through the channel increasing the light intensity at a back portion 2116 of the fluid sample 2102.

Figure 22:
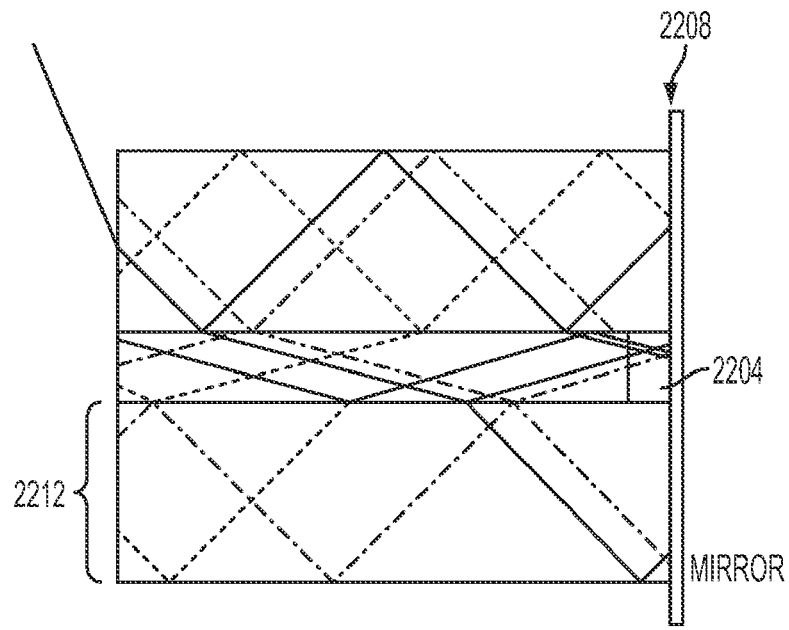

FIG. 22 shows one method of forming a mirror near the back portion of the sample. In practice, forming a highly reflective or mirrored surface adjacent to a thin fluid sample presents challenging fabrication problems. In FIG. 22, a solid but optically transparent material 2204 is formed near the back of the channel that confines the fluid sample. A coating 2208 deposited over optically transparent material 2204 forms a highly reflective surface to produce the mirror-like effect.

Figure 23:
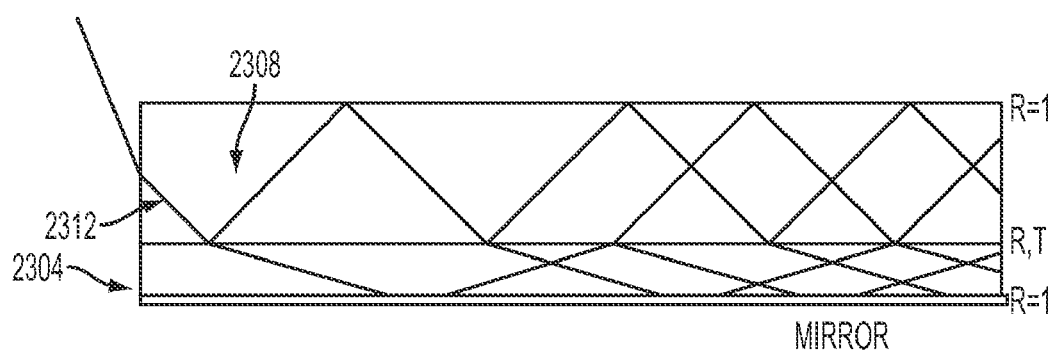

Using highly reflective surface such as mirrors to minimize light loss and/or improve light distribution though the sample is not limited to mirror placement at the back end of the sample. FIG. 23 shows further enhancing light confinement within the liquid layer by using a mirror surface 2304 as a bottom substrate.

As shown in FIG. 23, internal reflections 2308 from an incident beam 2312 in the cladding can be significant when coupling light into the fluid sample. Matching the indexes to minimize or otherwise adjust for such reflections can be difficult because the interface reflectivity between the top cladding layer and the fluid is highly dependent on the respective refractive indexes. However, the fluid index of refraction varies depending on the sample fluid being tested.

Figure 24:
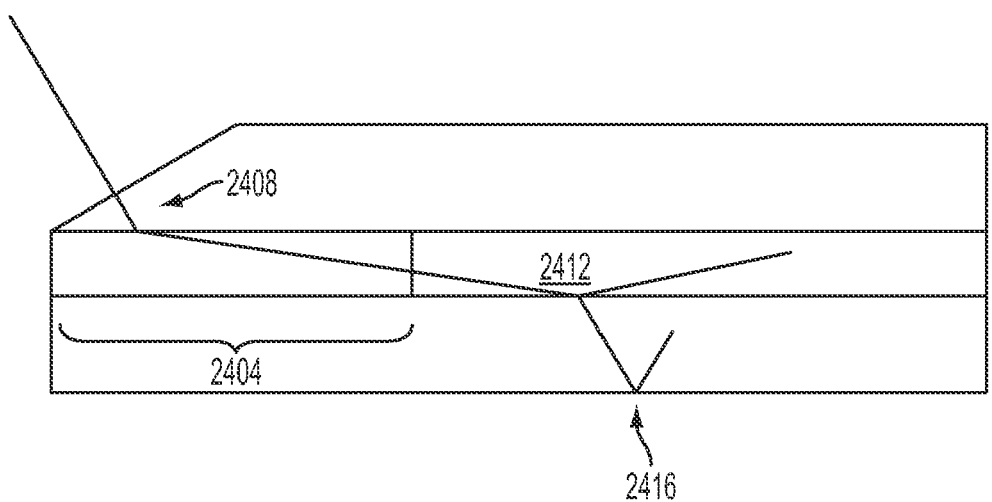
FIG. 24 shows a solid coupling zone used to minimize the effect of different sample indexes of refraction.

FIG. 24 shows one method of accommodating fluid index variations. In FIG. 24, a solid coupling zone material 2404 or "sample substitute" is positioned in the initial part or coupling zone region of the fluid layer 2406. As used herein, "coupling zone" is broadly defined to mean any region or segment of the cladding and sample (or sample substitute) that is designed to first receive light from the light source and to couple and distribute that light into the sample. The refractive index of the coupling zone material 2404 is constant. The known refractive index allows designs that assure light enters fluid layer 2406 almost parallel to the waveguide. Such large (around 70-110 degrees) angles of incidence from the coupling zone into a sample's varying refractive index assures that light is highly confined within the fluid. The coupling zone material characteristics are typically selected to (1) have a high transmission at the glass/coupling interface 2408, (2) have an index that closely matches that of the fluid in fluid channel 2412, (typically within 0.1 of the index of refraction of the fluid) and (3) maintain total internal reflection at the glass air interface 2416.

Figure 25:
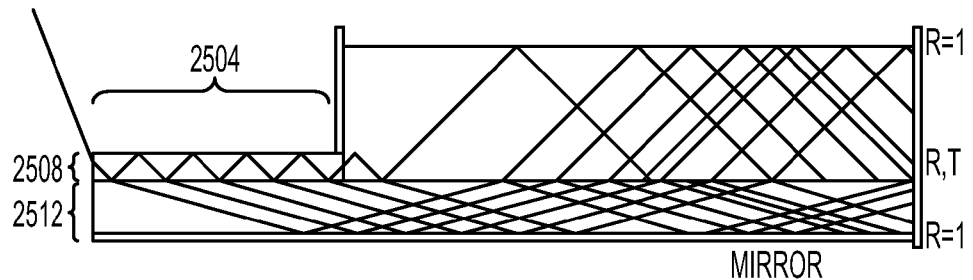
FIG. 25 shows using a thin coupling zone top layer to increase reflections in a top layer and thereby increase the homogeneity of the light in the material over a shorter distance.

FIG. 25 shows a coupling zone 2504 that uses a thinner cladding region in the coupling zone to quickly achieve a more approximately homogeneous light distribution along the fluid channel. The thinner cladding increases the number of reflections in the first cladding layer 2508 of coupling zone 2404. FIG. 25 shows thin cladding layer 2508 to be substantially thinner then the thickness of fluid layer 2512 in coupling zone 2404. Typically, the thin cladding layer thickness is less than 200 micrometers, or less than the thickness of the fluid layer and more typically less than one quarter the thickness of the remaining first cladding layer outside of the coupling zone. In one embodiment, the cladding layer thickness in the coupling zone may be 100 times the wavelength of the incident light. The thin cladding in coupling zone 2504 produces closely spaced reflections at the interface between the fluid and the first cladding layer 2508 thereby creating many entry points for the light to enter the fluid layer 2512. The many entry points produce a fairly uniform or almost homogenous distribution of light in the fluid sample over a fairly short distance (typically less than 5 millimeters).

Figure 26:
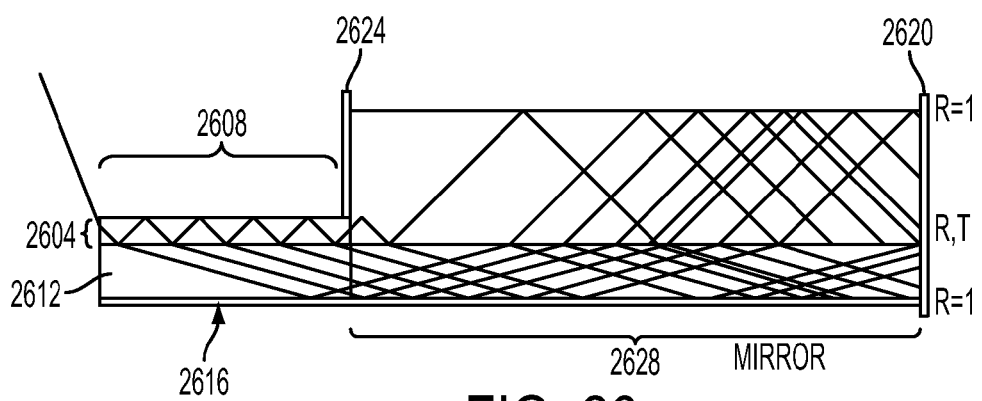
FIG. 26 shows a system utilizing a thin coupling zone as well as mirrors to improve light distribution in a sample.

FIG. 26 shows combining the various techniques described herein to achieve a uniform distribution of light in the fluid layer. The techniques include using a thinner cladding layer 2604 in a coupling zone 2608 and using a solid coupling zone material 2612 in the coupling zone 2608. In one embodiment, the solid coupling zone material 2612 is selected to have an index of refraction that is within 0.1 of the index of refraction of the analyte. The technique used may also use mirrored bottom 2616 and back 2620 surfaces. Typical reflectivities of the mirrored back surface exceed 80% and may even exceed 90% of the light at the wavelength range of light output by a light source. In the illustrated embodiment the thickness of cladding layer 2604 between the coupling zone and the body forms a discontinuity. A mirrored or other highly reflective surface 2624 coats the discontinuity between coupling zone 2608 cladding and body 2628 cladding to minimize light loss.

Figure 27:
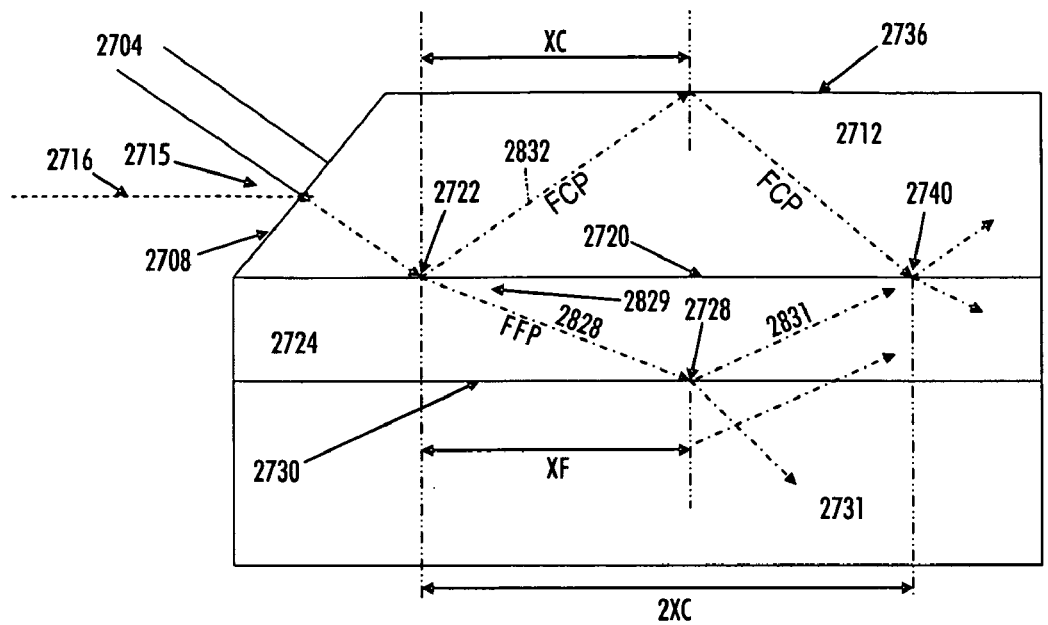
FIG. 27 shows optimizing light distributions by optimizing cladding and sample geometries as well as selecting appropriate indexes of refraction of the sample and cladding.

Uniform light distribution in the sample or fluid layer may be further enhanced by developing an appropriate relationship between the indexes of refraction of the cladding layer and the fluid layer, the thickness of the cladding layer and the fluid layer, and the initial direction of light propagation in the cladding layer. FIG. 27 shows an example relationship.

In FIG. 27, a portion or ray of light beam 2704 is shown normally incident on an angled edge 2708 of cladding layer 2712. In one embodiment, light beam 2704 is a laser beam. In the illustrated example, the angle of incidence with respect to a plane 2716 approximately parallel to an interface 2720 between cladding layer 2712 and liquid sample 2724 is approximately 27 degrees.

In cladding layer 2712, the portion of beam (hereinafter beam) reflects and refracts at point 2722 of interface 2720. Resulting refracted beam 2828 travels at a refracted angle 2829 defined by Snell's law. Thus angle 2829 is equal approximately to the arcsin (((index of cladding sin(angle of incidence))/index of liquid sample). After refracting at point 2722, the beam propagates a free fluid propagation (FFP) distance before being reflected at point 2728 of bottom interface 2730. As used herein, "free fluid propagation distance" is defined as the distance the beam travels in the fluid, usually a liquid, before the next reflection or refraction. In the illustrated example, the free fluid propagation distance is the distance between point 2728 and point 2722. The FFP has an X component designated "XE" along the X axis. The x axis component of the FFP can be determined by XF=FFPcos (angle of refraction).

Bottom interface 2730 is the interface between a bottom cladding layer 2731 and sample fluid 2724. The beam 2831 reflected at point 2728 along interface 2730 propagates another FFP distance prior to its next reflection/refraction at interface 2720. Assuming that interface 2730 and interface 2720 are parallel, and assuming a uniform index of refraction of the sample, the x axis component of beam 2831 is also XF. Thus the total x axis distance traveled by beam 2828 in the sample before returning to interface 2720 is 2XF.

Concurrent with the generation of refracted beam 2828, beam 2704 also produces a reflected beam 2832 at point 2722.

Reflected beam 2832 propagates a free cladding propagation (FCP) distance before reflecting off cladding boundary 2736 and traveling a second free cladding propagation distance to point 2740. As used herein, a "free cladding propagation distance" is defined as the distance a beam travels in the cladding before being reflected or refracted. The horizontal or x axis component of each FOP distance can be determined as XC=FCPcos(angle of incidence). The total x-axis distance between when a beam reflects from interface 2720 and returns to interface 2720 (illustrated as the distance between point 2440 l and point 2722) can be mathematically determined as 2XC or 2(FCP)cos(angle of incidence).(assuming a uniform cladding with parallel boundaries)

The reflections and refractions of each ray in the incident beam eventually forms a uniform or relatively homogenous light intensity distribution through the liquid sample after a "coupling distance" D along the X axis. As used herein, the coupling distance is defined as the distance after which intensity variations in the sample vary by less than 2%. The coupling distance is kept as short as possible to enhance light interactions. One way of shortening the coupling distance is to synchronize the light interactions at top interface 2720 such that the reflection/refraction from the beams in the cladding layer approximately coincide along the x direction with the reflection/refraction of beams in the sample, typically a liquid layer. Mathematically, this may be expressed as the ratio, 2XF/2XC being a rational number (a ratio between two integers). When a very highly collimated 1 mm diameter laser beam is coupled, and when XF=XC, a resulting coupling distance of 21mm can be achieved.

Further shortening of the coupling distance may be accomplished by creating a "rough" surfaces or "imperfections" at the sample-cladding interfaces. The imperfections improve light homogeneity, as long as the imperfections do not introduce significant losses. For example, a typical roughness would locally bend rays more than 0.02 degrees and up to 0.5 degrees, but would avoid "loosing" particular rays of light. In terms of height variations, the "roughness" or height variations are random and quite small, typically more than one time but less than 5 times the wavelength of the incident beam.

Returning to FIG. 1, once an ARGOW propagating wave is generated in the sample, the resulting interaction of the light with the sample contents may be analyzed for information. In one embodiment, a detector 140 of FIG. 1 detects the light that propagates through the sample. In an alternate embodiment, a detector 144 of FIG. 1 detects light that is scattered or refracted by the sample. Depending on the target (e.g. bioagent) to be detected and the particular detection technique to be used, detectors 140, 144 may include wavelength sensitive elements such as gratings, prisms, Bragg reflectors or resonators.

Wavelength sensitive elements enable identification of signatures and specific biological or chemical agents. Detectors 140, 144 may also integrate the wavelength sensitive elements with conventional optics or micro-optics components including mirrors and lenses. In some embodiments, the detectors may include a means for converting the optical signal to an electrical signal. Such conversions may be achieved using a charge coupled device, a photosensor, or any of a variety of conversion devices. Once converted to an electrical signal, detector 140, 144 output can be analyzed using electric processors, such as microprocessors (not shown).

Detector 140 of FIG. 1 detects light transmitted by sample 116. In one embodiment, the light transmitted by sample 116 is analyzed by processors coupled to the detector to determine the presence or absence of chemical, environmental or biological molecules in sample 116. The output of detector 140 may also be used to analyze the characteristics of molecules in sample 116. An example of using detectors to detect light transmitted by a sample and a processor to analyze the detector output is provided in U.S. Pat. No. 6,603,548 entitled "Biosensor" by Church et al. which is hereby incorporated by reference in its entirety.

In an alternate embodiment, instead of detecting light that is transmitted, a second detection system such as detector array 144 may detect light that is scattered or otherwise output by sample 116. Scattered light may be caused by reflection or refraction of light by molecules in sample 116. Example scattering techniques include elastic and inelastic light scattering spectroscopy as described in Introduction to Biophotonics, by Paras N. Prasad ISBN 0-471-28770-9, Wiley-Interscience 2003) which is hereby incorporated by reference in its entirety.

In still another embodiment, light output from sample 116 may be caused by fluorescence that results from binding of chemical elements in the sample to biological materials. The binding results in fluorescence when an excitation source, such as the anti-resonant light propagating in the sample is present. U.S. Pat. No. 6,577,780 by Lockhart entitled Cell Designs for Optical Sensors describes using antigens that attach to antibodies resulting in a structure that fluoresces in the presence of an evanescent field. U.S. Pat. No. 6,577,780 by Lockhart is hereby incorporated by reference in its entirety. By using anti-resonant waves propagating through the sample instead of evanescent fields, the sensitivity of the system can be improved.

Besides the examples given, many other optical detection and sensing techniques may be used with sensors 140 and 144. Those techniques include, but are not limited to single or multi-color light-induced intrinsic fluorescence or fluorescence from tagged molecules and applications derived from the manipulation of the fluorescent lights such as fluorescence lifetime imaging microscopy (FLIM), fluorescence resonance energy transfer (FRET), fluorescence correlation spectroscopy (FCS), etc., light scattering or vibrational spectroscopy (Raman, IR) or spectroscopic applications utilizing optical activity of chiral media such as circular dichroism (CD), among others. A more detailed description of various detection techniques utilizing photon interactions is provided in Chapter 4 of "*Introduction to Biophotonics*" by Paras N. Prasad, ISBN 0-471-28770-9, Wiley-Intersicence 2003) which is hereby incorporated by reference.

Although optical detection techniques have been described, other methods of detecting the enhanced light-target interaction may be used. For example thermal detection techniques may be used. Predetermined light wavelengths may initiate a specific exothermic or endothermic chemical reaction which causes a temperature change. The detected temperature change indicates the presence of the reaction and thus the presence of compounds needed to create the reaction. Other example detection techniques include, but are not limited to, ARGOW induced photo ionization or photo fractionation. The photo ionization or photo fractionation generates charged particle which can be detected by known means such as a Coulter Counter.

In order to speed up analysis of the samples, parallel processing of a sample may occur. Thus the techniques described are not mutually exclusive and may be used in conjunction or in parallel to yield rapid detailed analysis of molecules in the sample.

A number of example geometries for a sample geometry, sample states and analysis techniques have been provided. However, the details provided have been provided as examples to facilitate understanding of the invention, and to provide sample calculations. However, the scope of the invention should not be limited to these geometries nor the particular analysis techniques described. For example, the geometries may be altered, the sample may be a liquid, solid or gas, the analysis techniques may use alternate detections systems. Thus, the invention should only be limited by the claims, as originally presented and as they may be amended to encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. An apparatus for analyzing a sample containing a target analyte comprising:
   a sample including a target analyte, the sample having a analyte index of refraction;
   a first layer adjacent at least one side of the sample, the first layer including a coupling zone followed by a thicker region, the first layer having first index of refraction greater than the analyte index of refraction;
   a second layer adjacent at least a second side of the sample, the second layer having a second index of refraction, the second index of refraction greater than the analyte index of refraction;
   the coupling zone to receive light from a light source and generate an approximately homogenous anti-resonant guided optical mode in the sample; and,
   an analyzing system to detect the interaction of the light propagating in the sample with the target analyte.

2. The apparatus of claim 1 wherein the coupling zone has a thickness less than 100 times the wavelength of light from the light source.

3. The apparatus of claim 1 wherein the thickness of the first layer in the coupling zone is less than the thickness of the sample in the coupling zone.

4. The apparatus of claim 1 wherein the second layer includes a surface having a reflectivity exceeding 90% at the frequencies of light output by the light source.

5. The apparatus of claim 1 wherein the thickness of the first layer forms a discontinuity between the coupling region and the thicker region, the discontinuity_coated with a surface having a reflectivity exceeding 80% at the frequencies of light output by the light source.

6. The apparatus of claim 1 wherein the coupling zone includes a solid coupling zone material between the first layer and the second layer, the index of refraction of the solid selected to be within 0.1 of the index of refraction of the analyte.

7. The apparatus of claim 1 wherein the first layer includes a curved surface that distributes the light entering the first layer from the light source.

8. The apparatus of claim 7 wherein the curved surface is concave.

9. The apparatus of claim 1 wherein a plurality of lenses focuses the light from the light source prior to input of the light into the first layer.

10. The apparatus of claim 9 wherein the lens system creates an angular spectrum of light rays that are wider in a first direction and narrower in a second direction, the angular spectrum causing propagation of light within the first and second layer and the sample under a variety of angles such that the average of all light rays produces a homogeneous light distribution in the sample in the direction parallel to the waveguide.

11. The apparatus of claim 1 wherein the first layer is made from a glass material.

12. A method of introducing light into a target analyte layer comprising:
   generating light at a light source and inputting the light into a first cladding layer in a coupling zone, the first cladding layer in the coupling zone thinner than a thickness of the first cladding layer outside of the coupling zone; and,
   inducing multiple reflections in the first cladding layer at an interface between the analyte layer and the first cladding layer, each reflection inputting a fraction of the incident light into the analyte layer to create a distributed light intensity in the analyte.

13. The method of claim 12 wherein the distributed light intensity creates an approximately homogeneous distribution of light in the analyte layer.

14. The method of claim 12 further comprising the operation of:
   focusing the light using a lens system prior to inputting the light into the first cladding layer.

15. The method of claim 12 further comprising the operation of creating slight deviations in reflection and refraction of adjacent rays at the cladding layer and analyte layer interface, the slight bending between 0.02 and 0.5 degrees caused by slight roughness of the cladding layer and analyte layer interface.

16. An apparatus for analyzing a sample including a target analyte comprising:
   a region for confining a sample including a target analyte, the sample having an anticipated analyte index of refraction;
   a first layer adjacent at least one side of the sample, the first layer including a coupling zone followed by a thicker region, the first layer having first index of refraction greater than the anticipated analyte index of refraction;
   a second layer adjacent at least a second side of the region for confining the sample, the second layer having a second index of refraction, the second index of refraction greater than the anticipated analyte index of refraction; and,
   the coupling zone to receive light from a light source and generate an approximately homogenous anti-resonant guided optical mode in the sample.

17. The apparatus of claim 16 further comprising:
   an analyzing system to detect the interaction of the light propagating in the sample with the target analyte.

18. The apparatus of claim 16 wherein a boundary between the region for coupling a sample and the first layer has a small apparently random variations in the boundary surface causing height differentials of greater than one time but less than five times a wavelength of light output by the light source, the variations to cause slight deviations in reflection and refraction of adjacent rays at the a cladding layer and analyte layer interface, the slight deviations between 0.02 and 0.5 degrees of the sample and first layer interface.

19. A method of inputting light for analyzing a sample including a target analyte comprising:
   inputting light into a cladding layer with a cladding index of refraction;
   reflecting and refracting light at a cladding and sample interface, the reflected light reflected at a reflected angle and the refracted light refracted at a refracted angle with respect to the interface;
   adjusting angle of incidence such that XF =(free fluid propagation distance)cos(angle of refraction) XC=(free cladding propagation distance) cos(angle of reflection) and 2XF divided by 2XC is equal to a ratio between two integers.

20. The method of claim 19 wherein the rational number is approximately one.

21. The method of claim 19 wherein the fluid is a liquid.

22. The method of claim 19 wherein the fluid is a gas.

* * * * *

UNITED STATES PATENT AND TRADEMARK OFFICE
CERTIFICATE OF CORRECTION

| | | |
|---|---|---|
| PATENT NO. | : 7,456,953 B2 | Page 1 of 1 |
| APPLICATION NO. | : 11/777976 | |
| DATED | : November 25, 2008 | |
| INVENTOR(S) | : Oliver Schmidt et al. | |

It is certified that error appears in the above-identified patent and that said Letters Patent is hereby corrected as shown below:

Column 1, line 12, insert as a new paragraph:

--This invention was made with Government support under N00014-05-C-0430 awarded by ONR. The Government has certain rights in this invention.--

Signed and Sealed this

Fourteenth Day of April, 2009

JOHN DOLL
*Acting Director of the United States Patent and Trademark Office*